US012697445B2

(12) United States Patent
Kahl et al.

(10) Patent No.: US 12,697,445 B2
(45) Date of Patent: Aug. 4, 2026

(54) METHOD AND DEVICE FOR THE INSPECTION OF A CONDITION OF A CANNULA MOUNTED ON A SYRINGE

(71) Applicant: WILCO AG, Wohlen (CH)

(72) Inventors: Matthias Kahl, Lörrach (DE); Christian Stirnimann, Dielsdorf (CH)

(73) Assignee: WILCO AG, Wohlen (CH)

( * ) Notice: Subject to any disclaimer, the term of this patent is extended or adjusted under 35 U.S.C. 154(b) by 721 days.

(21) Appl. No.: 17/268,700

(22) PCT Filed: Aug. 6, 2019

(86) PCT No.: PCT/EP2019/071144
§ 371 (c)(1),
(2) Date: Feb. 16, 2021

(87) PCT Pub. No.: WO2020/035355
PCT Pub. Date: Feb. 20, 2020

(65) Prior Publication Data
US 2021/0228821 A1 Jul. 29, 2021

(30) Foreign Application Priority Data
Aug. 16, 2018 (CH) .................................... 00995/18

(51) Int. Cl.
*A61M 5/50* (2006.01)
*A61M 5/158* (2006.01)
(Continued)

(52) U.S. Cl.
CPC ........ *A61M 5/5086* (2013.01); *A61M 5/3202* (2013.01); *G01N 27/82* (2013.01);
(Continued)

(58) Field of Classification Search
CPC .... A61M 5/5086; A61M 5/3202; A61M 5/32; A61M 2005/1588; A61M 2205/3317;
(Continued)

(56) References Cited

U.S. PATENT DOCUMENTS 4,063,561 A * 12/1977 McKenna ............. A61M 16/04
128/207.15
8,861,677 B2 * 10/2014 Gray ..................... G06T 7/0004
378/62
(Continued)

FOREIGN PATENT DOCUMENTS

DE 19806971 C1 6/1999
DE 102007040488 A1 3/2009
(Continued)

OTHER PUBLICATIONS

Nov. 29, 2019 Search Report issued International Patent Application No. PCT/EP2019/071144.
(Continued)

*Primary Examiner* — Michael J Tsai
*Assistant Examiner* — Forrest B Dipert
(74) *Attorney, Agent, or Firm* — Oliff PLC

(57) ABSTRACT

A method for the inspection of a condition, in particular for the detection of defects, of a cannula (or injection needle) mounted on a syringe, which is located under a protective cap, and devices for carrying out such methods. A method includes measuring a magnetic field, in particular a magnetic field distribution, in the vicinity of the cannula. The presence of a ferromagnetic cannula causes a local change in the course of the magnetic field lines. This can be measured and used to determine whether the cannula, as desired, is arranged straight and coaxially to the syringe longitudinal axis, or whether it has a defect, such as being bent, kinked, compressed, broken/severed, oblique to the longitudinal axis
(Continued)

of the syringe or eccentric to the longitudinal axis of the syringe.

18 Claims, 2 Drawing Sheets

(51) Int. Cl.
  *A61M 5/32*      (2006.01)
  *G01N 27/82*     (2006.01)
  *G01R 33/02*     (2006.01)

(52) U.S. Cl.
  CPC ..... *G01R 33/02* (2013.01); *A61M 2005/1588* (2013.01); *A61M 5/32* (2013.01); *A61M 2205/0272* (2013.01); *A61M 2205/3317* (2013.01); *A61M 2205/6054* (2013.01); *A61M 2209/02* (2013.01)

(58) Field of Classification Search
  CPC .. A61M 2205/0272; A61M 2205/6054; A61M 2209/02; G01N 27/82; G01R 33/02
  See application file for complete search history.

(56)                References Cited

U.S. PATENT DOCUMENTS

| | | | |
|---|---|---|---|
| 10,032,552 B2 * | 7/2018 | Ma | A61B 34/20 |
| 2012/0307972 A1 | 12/2012 | Gray et al. | |
| 2013/0242082 A1 | 9/2013 | Miller | |
| 2015/0306319 A1 * | 10/2015 | Nessel | A61M 5/24 604/111 |

FOREIGN PATENT DOCUMENTS

| | | | |
|---|---|---|---|
| DE | 102008040488 A1 | 1/2010 | |
| EP | 0 941 742 A2 | 9/1999 | |
| EP | 2 939 601 A2 | 11/2015 | |
| JP | H02-203269 A | 8/1990 | |
| JP | 2016105046 A * | 6/2016 | |
| WO | 2013/050535 A2 | 4/2013 | |
| WO | WO-2018013843 A1 * | 1/2018 | A61B 5/4839 |

OTHER PUBLICATIONS

Nov. 29, 2019 Written Opinion issued International Patent Application No. PCT/EP2019/071144.

* cited by examiner

METHOD AND DEVICE FOR THE INSPECTION OF A CONDITION OF A CANNULA MOUNTED ON A SYRINGE

FIELD OF THE INVENTION

The present invention relates to methods for the inspection of a condition, in particular for the detection of defects, of a cannula (or injection needle) mounted on a syringe, and to devices for carrying out such methods.

BACKGROUND OF THE INVENTION

During the manufacture of medical syringes, when the non-transparent protective cap (needle shield) is put on, the cannula or needle underneath may be bent or compressed, pierce the protective cap or even break. In this way, the needle not only becomes a danger to the user, but can also lose its sterility. Today, different methods are used to detect such damage. For example, classical image processing is used to detect the position of the protective cap. However, this method sorts out a relatively high proportion of good syringes (high "false rejection rate"). Probably the most reliable method at present is based on X-raying each syringe and on automatic analysis of the X-ray images taken. However, this technology is rather complex; for example, the X-ray area must be shielded from the outside, which is very cost-intensive. In addition, the product can be stressed by the X-ray radiation. Alternatively, there is high-voltage testing. In this process, an electrode under high voltage is held against the end with the protective cap. If the cannula pierces through the protective cap, this can be detected with the high voltage test. However, bent, compressed or broken needles that are under an intact protective cap cannot be reliably detected.

There is therefore a need for means which allow simple (and consequently cost-effective) and reliable detection of defects on a needle mounted on a syringe. In order to be used in inspection machines with a high throughput of test items, such as around 600 syringes per minute, the means must also be able to inspect the individual test items very quickly with a high degree of reliability.

SUMMARY OF THE INVENTION

It is an object of the present invention to provide a method for rapid, reliable and inexpensive inspection of a condition, in particular for the detection of defects, of a cannula mounted on a syringe. According to the invention, this object is fulfilled by the inspection method defined in claim 1.

It is also an object of the present invention to propose a corresponding device for the rapid, reliable and inexpensive inspection of a condition, in particular for the detection of defects, of a cannula mounted on a syringe. According to the invention, this object is solved by the inspection device defined in claim 11.

Specific embodiments according to the invention are given in the dependent claims.

A method according to the invention for inspecting a condition, in particular for detecting certain defects, of a cannula mounted on a syringe, which is located in a cannula protective cap, comprises measuring a magnetic field, in particular a magnetic field distribution, in a vicinity of the cannula.

In one embodiment variant of the method, one or more magnetic field sensors, in particular an induction sensor, a fluxgate magnetometer, a Hall sensor, a magnetoresistive sensor, such as an AMR (anisotropic magnetoresistive), CMR (colossal magnetoresistance), GMR (giant magnetoresistance) or TMR (tunnel magnetoresistance) sensor, are used for measuring the magnetic field, in particular the magnetic field distribution.

In a further embodiment variant of the method, the one or more magnetic field sensors are designed as one-, two- or three-axis magnetic field sensors in order to measure the magnetic field, in particular the magnetic field distribution, in one, two or three dimensions.

In another embodiment variant of the method, to measure the magnetic field, in particular the magnetic field distribution, the cannula is moved relative to the one or more magnetic field sensors, in particular rotating the syringe about its longitudinal axis and/or moving it along its longitudinal axis, or moving the one or more magnetic field sensors parallel to the longitudinal axis of the syringe.

In another embodiment variant of the method, one or more motors, such as servo motors or stepper motors, are used to rotate and/or move the syringe longitudinally, wherein a gear is used such that the rotational frequency of the one or more motors is a multiple or a fraction of the rotational frequency of the syringe. This prevents magnetic fields generated by the one or more motors from interfering with the magnetic field to be measured in the vicinity of the cannula or the magnetic field distribution to be measured.

In a further embodiment variant of the method, the magnetic field is generated, at least in part by the earth ⟨S⟩ magnetic field, by an arrangement comprising one or more permanent magnets, or by an arrangement comprising one or more electromagnets, such as a Helmholtz coil, wherein the arrangement especially also comprises one or more iron cores.

In another embodiment variant of the method, a magnetic shield is used to suppress magnetic interference fields.

In a further embodiment variant, the method comprises a comparison of the measured magnetic field, in particular the measured magnetic field distribution, for the cannula with the measured magnetic field, in particular the measured magnetic field distribution, for a reference syringe having an attached/mounted reference cannula located in a cannula protective cap having a target condition, and determining the condition of the cannula mounted on the syringe based on the comparison.

In a further embodiment variant of the method, the determination of the condition of the cannula mounted on the syringe is based on comparing an amplitude and/or phase position of the measured magnetic field for the reference cannula with an amplitude and/or phase position of the measured magnetic field for the cannula.

In a further embodiment variant of the method, the determination of the condition of the cannula mounted on the syringe is based on a comparison of an amplitude and/or phase position of the measured magnetic field at two different locations, which is measured e.g. with two magnetic field sensors arranged offset to each other.

In a further embodiment variant, the method comprises transforming a measured time course of the magnetic field, in particular the magnetic field distribution, from the time domain to the frequency domain.

In a further embodiment variant, the method comprises determining a frequency component of the magnetic field, in particular the magnetic field distribution, at a rotation frequency of the syringe, in particular also at twice the rotation frequency of the syringe, e.g. by means of a discrete Fourier transformation (DFT).

In a further embodiment variant of the method, the condition of the cannula is at least one of straight, bent, kinked, compressed, broken/severed, coaxial with respect to the longitudinal axis of the syringe, oblique with respect to the longitudinal axis of the syringe, eccentric with respect to the longitudinal axis of the syringe.

According to another aspect of the present invention, a device for the inspection of a condition of a cannula mounted on a syringe, which is located in a cannula protective cap, comprises one or more magnetic field sensors, in particular an induction sensor, a fluxgate magnetometer, a Hall sensor, a magnetoresistive sensor, such as an AMR (anisotropic magnetoresistive), CMR (colossal magnetoresistance), GMR (giant magnetoresistance) or TMR (tunnel magnetoresistance) sensor, for measuring a magnetic field, in particular a magnetic field distribution, in a vicinity of the cannula.

In a further embodiment variant of the device, the one or more magnetic field sensors are designed as one-, two- or three-axis magnetic field sensors in order to measure the magnetic field, in particular the magnetic field distribution, in one, two or three dimensions.

In a further embodiment variant, the device further comprises means for moving the cannula relative to the one or more magnetic field sensors, in particular for rotating the syringe about its longitudinal axis and/or for moving the syringe along its longitudinal axis, or for moving the one or more magnetic field sensors parallel to the longitudinal axis of the syringe.

In another embodiment variant, the device further comprises one or more motors, such as servo or stepper motors, for rotating and/or longitudinally moving the syringe, wherein a gear is used such that the rotational frequency of the one or more motors is a multiple or fraction of the rotational frequency of the syringe.

In a further embodiment variant, the device further comprises an arrangement having one or more permanent magnets and/or an arrangement having one or more electromagnets, such as a Helmholtz coil, for generating a magnetic field, wherein the arrangement in particular also comprises one or more iron cores.

In another embodiment variant, the device further comprises a magnetic shield for suppressing magnetic interference fields.

In a further embodiment variant, the device further comprises a comparator unit for comparing the measured magnetic field, in particular the measured magnetic field distribution, for the cannula with the measured magnetic field, in particular the measured magnetic field distribution, for a reference syringe with an attached/mounted reference cannula located in a cannula protective cap having a target condition, and for determining the state of the cannula mounted on the syringe based on the comparison.

In a further embodiment variant of the device, the comparator unit is designed to perform a comparison of an amplitude and/or phase position of the measured magnetic field for the reference cannula with an amplitude and/or phase position of the measured magnetic field for the cannula, and to determine therefrom the condition of the cannula mounted on the syringe.

In a further embodiment variant, the device further comprises a unit for performing a transformation of a measured temporal progression of the magnetic field, in particular of the magnetic field distribution, from the time domain to the frequency domain.

In a further embodiment variant, the device further comprises an output, in particular for providing an output signal, which is configured to indicate the state of the cannula as at least one of straight, bent, kinked, compressed, broken/severed, coaxial to the syringe longitudinal axis, oblique to the syringe longitudinal axis, eccentric to the longitudinal axis of the syringe.

In a further embodiment variant of the device, several magnetic field sensors are arranged vertically one above the other along an axis, in particular equidistantly spaced, wherein the axis is arranged laterally parallel to the longitudinal axis of the syringe to be inspected.

In another embodiment variant, the device comprises a Helmholtz coil consisting of two coaxially arranged coils whose coil axis is arranged horizontally to generate the magnetic field in the horizontal direction, with the syringe for inspection being arranged between the two coils.

It should be noted that combinations of the above embodiment variants are possible, which in turn lead to more specific embodiments of the present invention.

BRIEF DESCRIPTION OF THE DRAWINGS

Non-limiting exemplary embodiments of the present invention are explained in further detail below with reference to figures, wherein.

In the figures, the same reference numerals stand for the same elements.

DETAILED DESCRIPTION OF THE INVENTION

In the assembly process of medical syringes, such as single-use insulin syringes, the cannula or injection needle is mounted on or attached to the syringe, e.g. glued in place, and then a protective cap is mounted on or attached to the cannula. The cannula must penetrate the material of the protective cap.

Accordingly, this process takes place with a certain force, so that the cannula can be bent, kinked, compressed, or can break or break off. These defects pose a multiple risk, e.g. there is a risk of injury during use and/or sterility is no longer ensured.

Figure 1:
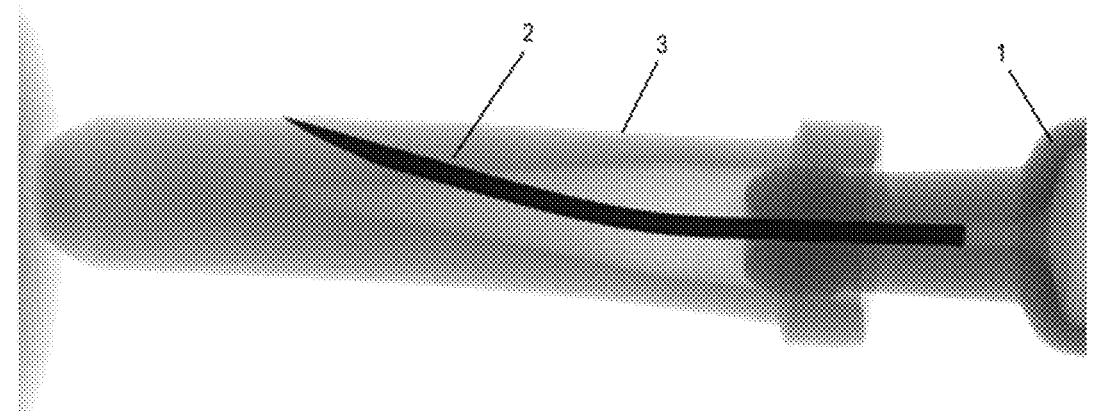
FIG. 1 shows an X-ray image (according to the prior art) of a syringe with a protective cap in place, under which there is a bent cannula.

FIG. 1 shows an X-ray image of a syringe 1 with a mounted/attached optically opaque protective cap 3, under which a bent cannula 2 is located, as recorded in a prior art process.

The present invention utilizes the effect that ferromagnetic materials influence an external magnetic field in their environment. Thus, ferromagnetic materials tend to draw magnetic fields into themselves. The field lines of an external magnetic field end on the surface of the ferromagnetic body and run inside it. Thus, the presence of a steel injection needle causes a local change in the course of the magnetic field lines. An intact, i.e. straight needle will cause a different change in the magnetic field lines than a needle which has a kink, for example.

Figure 2:
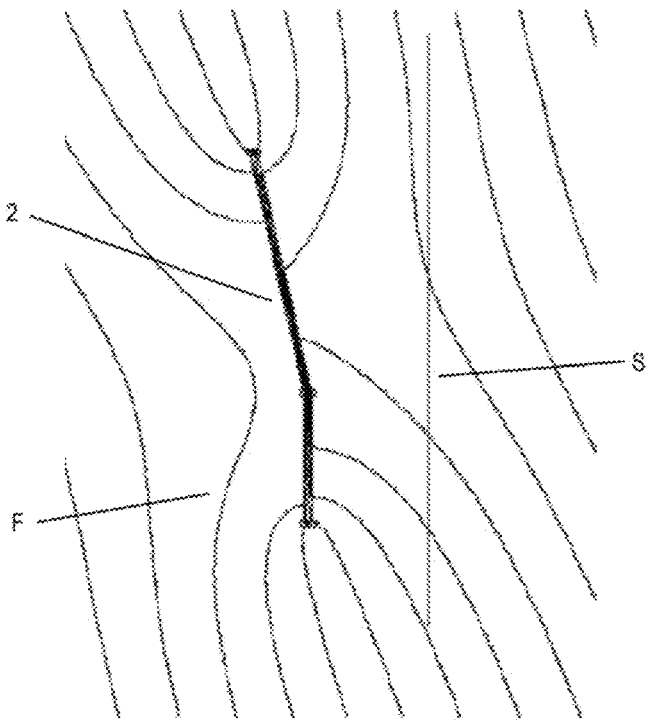
FIG. 2 shows an example of the field line progression of the earth's magnetic field (with an inclination of 64°) in the vicinity of a curved steel injection needle.

FIG. 2 schematically illustrates an example of the field line progression F of the earth's magnetic field in the vicinity of a bent injection needle or cannula 2.

Depending on the latitude, the earth's magnetic field inclines differently in the direction of the earth. For example, the earth's magnetic field shown in FIG. 2 has an inclination of 64° downward corresponding to the 47th degree of latitude. The magnetic field lines F are focused by the steel injection needle 2 and the field lines further out are deflected towards the injection needle 2. This deformation of the field lines compared to the case where the injection needle 2 is straight can be detected by measuring the magnetic field, in particular the magnetic field distribution, in a vicinity of the cannula 2. Based on the measurement of the magnetic field at one or more points, e.g. on or along the measuring section S, it is then possible to infer the condition of the cannula 2, i.e., whether it has a particular defect such as a kink.

One or more magnetic field sensors, such as an induction sensor, a fluxgate magnetometer, a Hall sensor, a magnetoresistive sensor, such as an AMR (anisotropic magnetoresistive), CMR (colossal magnetoresistance), GMR (giant magnetoresistance) or TMR (tunnel magnetoresistance) sensor, can be used to measure the magnetic field or the magnetic field distribution. These magnetic field sensors can be designed as one-, two- or three-axis magnetic field sensors to measure the magnetic field or the magnetic field distribution in one, two or three dimensions. In this process, the cannula 2 can be moved relative to one or more magnetic field sensors, or conversely one or more magnetic field sensors can be moved relative to the cannula 2, e.g. vertically along the measuring section S, so that the magnetic field or the magnetic field distribution can be determined over the entire length of the cannula 2.

Figure 3:
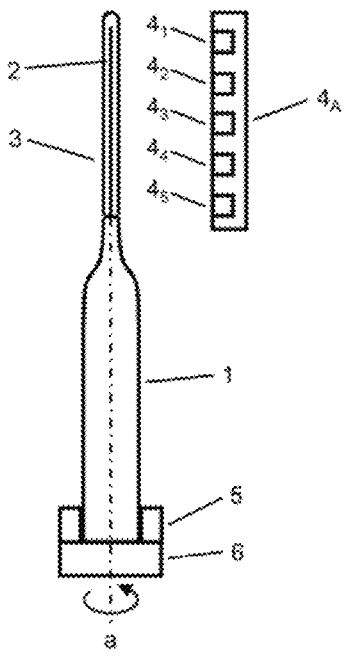
FIG. 3 shows a schematic side view of an embodiment variant of a device according to the invention.

FIG. 3 shows a schematic side view of an embodiment variant of a device for inspecting injection needles according to the invention. The syringe 1 is clamped in a syringe holder 5, which is arranged on a rotating device 6, by means of which the syringe 1 can be rotated about its longitudinal axis a. As a result of the rotation, the cannula 2 periodically changes the earth's magnetic field in the vicinity of the cannula 2. The earth's magnetic field is measured with the aid of the magnetic field sensor arrangement $4_A$, which consists of five magnetic field sensors $4_1$, □, $4_5$, which are arranged vertically one above the other parallel to the longitudinal axis a of the syringe. Alternatively, a single magnetic field sensor could also be used, which is moved up or down along the measuring section S.

The time course of the measured magnetic field is then transformed into the frequency domain. This can be carried out for individual frequencies e.g. by means of discrete Fourier transformation. The rotation frequency of the syringe 1 and its second harmonic (=double rotation frequency) are particularly relevant here. If the cannula 2 has a kink, the magnetic field is directed through it once per rotation in the direction of the magnetic field sensor arrangement $4_A$, i.e. closer to it, so that the magnetic field strength periodically increases and decreases at the rotation frequency. The distribution of the magnetic field along the cannula 2 will therefore have a larger maximum at the rotation frequency for the kinked tip than for a straight cannula 2. Also, due to the kink, there will be a different phase position of the magnetic field compared to the situation with a straight cannula 2. Based on the amplitude and/or phase position of the measured magnetic field, it is therefore possible to draw conclusions about the condition of the cannula 2, in particular when this is compared with the previously measured magnetic field in the vicinity of an intact, i.e. straight, reference cannula 2. The difference in the phase of the magnetic field at two spaced magnetic field sensors $4_{1□5}$ (e.g. two adjacent magnetic field sensors $4_i$ & $4_{i-1}$ of the magnetic field sensor arrangement $4_A$) can also be used as the phase position.

During measurements, notice should be taken to avoid magnetic interference fields. For example, electric servomotors generate such interference fields, which are modulated with the speed of the servomotor. To minimize their influence on the measurements, a gear can be used, for example, so that syringe 1 rotates many times faster or slower than the servomotor. For example, if the speed of the servomotor is three times the speed of rotation of the syringe (i.e., gear ratio 3:1), the magnetic field to be measured at the rotation frequency of syringe 1 will be hardly disturbed by the interference field generated by the servomotor at three times the rotation frequency of syringe 1. Alternatively, a magnetic shield can be used to suppress magnetic interference fields.

Instead of using the earth's magnetic field for the measurements, a magnetic field formed by an arrangement with one or more permanent magnets, or by an arrangement with one or more electromagnets, such as a Helmholtz coil, can also be used, wherein the arrangement can in particular also have one or more iron cores. In this way, for example, a strong homogeneous magnetic field can be generated.

Figure 4:
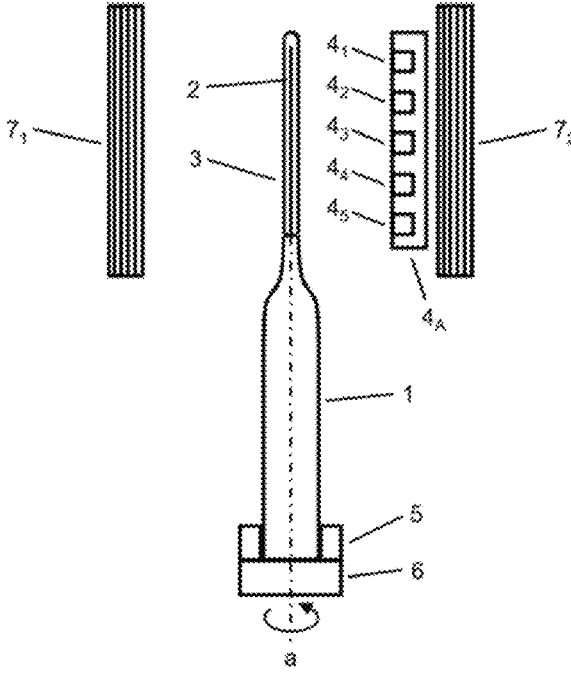
FIG. 4 shows a schematic side view of a further embodiment variant of a device according to the invention with a Helmholtz coil.

FIG. 4. schematically shows a side view of such an embodiment variant with a Helmholtz coil. One coil each of the Helmholtz coil pair $7_1$, $7_2$ is arranged to the left and right of the cannula 2 to be inspected. A homogeneous, horizontally aligned magnetic field is formed between the two coils $7_1$, $7_2$, which (as in FIG. 3) can be measured with the magnetic field sensor arrangement $4_A$.

LIST OF REFERENCE NUMERALS

1 Syringe
2 Cannula, needle
3 Cannula protective cap
$4_{1□5}$ Magnetic field sensor
$4_A$ Magnetic field sensor arrangement with several magnetic field sensors
5 Syringe holder
6 Rotating device (optionally with lifting device)
$7_{1,2}$ Helmholtz coil
a Syringe longitudinal axis
F Magnetic field line
S Sensor line, measuring section

The invention claimed is:

1. Method for inspecting a condition of a cannula which is mounted on a syringe and located in a cannula protective cap, comprising:
   introducing the cannula into a magnetic field;
   measuring said magnetic field in a vicinity of the cannula to obtain a measured magnetic field for the cannula; and
   determining a deformation of the magnetic field, caused by said introducing the cannula into the magnetic field, compared to a case where the cannula is a straight cannula.

2. Method according to claim 1, wherein one or more magnetic field sensors are used to measure the magnetic field.

3. Method according to claim 2, wherein the one or more magnetic field sensors are designed as one-, two- or three-axis magnetic field sensors adapted to measure the magnetic field in one, two or three dimensions.

4. Method according to claim 2, wherein for measuring the magnetic field the cannula is moved relative to the one or more magnetic field sensors, wherein the syringe is rotated about its longitudinal axis and/or moved along its longitudinal axis, or the one or more magnetic field sensors are moved parallel to the longitudinal axis of the syringe.

5. Method according to claim 1, wherein the magnetic field is generated, at least in part by the earth's magnetic field, by an arrangement comprising one or more permanent magnets, or by an arrangement comprising one or more electromagnets, wherein the arrangement comprising one or more electromagnets also comprises one or more iron cores.

6. Method according to claim 1, wherein a magnetic shield is used to suppress magnetic interference fields.

7. Method according to claim 1, comprising a comparison of the measured magnetic field for the cannula with a measured magnetic field for a reference syringe with a mounted reference cannula located in a cannula protective cap having a desired condition, and a determination of the condition of the cannula mounted on the syringe based on the comparison.

8. Method according to claim 7, wherein the determination of the condition of the cannula mounted on the syringe is based on a comparison of an amplitude and/or phase position of the measured magnetic field for the reference cannula with an amplitude and/or phase position of the measured magnetic field for the cannula.

9. Method according to claim 1, comprising a transformation of a measured time course of the magnetic field from a time domain to a frequency domain.

10. Method according to claim 1, wherein the condition of the cannula is at least one of straight, bent, kinked, compressed, broken/severed, coaxial to a longitudinal axis of the syringe, oblique to the longitudinal axis, eccentric to the longitudinal axis.

11. Device for inspecting a condition of a cannula which is mounted on a syringe and located in a cannula protective cap, comprising:

one or more magnetic field sensors for measuring a magnetic field in a vicinity of the cannula, after the cannula has been introduced to said magnetic field, to obtain a measured magnetic field for the cannula; and a comparator adapted to compare, based on a deformation of the magnetic field caused by said introducing the cannula into the magnetic field, the measured magnetic field for the cannula with a measured magnetic field for a reference syringe with a mounted reference cannula located in a cannula protective cap having a desired condition and to determine the condition of the cannula mounted on the syringe based on the comparison.

12. Device according to claim 11, wherein the one or more magnetic field sensors are designed as one-, two- or three-axis magnetic field sensors adapted to measure the magnetic field in one, two or three dimensions.

13. Device according to claim 11, further comprising a means for moving the cannula relative to the one or more magnetic field sensors for rotating the syringe about its longitudinal axis and/or for moving the syringe along its longitudinal axis, or for moving the one or more magnetic field sensors parallel to the longitudinal axis of the syringe.

14. Device according to claim 11, further comprising an arrangement having one or more permanent magnets and/or an arrangement having one or more electromagnets for generating a magnetic field, wherein the arrangement comprising one or more electromagnets also comprises one or more iron cores.

15. Device according to claim 11, further comprising a magnetic shield for suppressing magnetic interference fields.

16. Device according to claim 11, wherein the comparator is designed to perform a comparison of an amplitude and/or phase position of the measured magnetic field for the reference cannula with an amplitude and/or phase position of the measured magnetic field for the cannula, and to determine therefrom the condition of the cannula mounted on the syringe.

17. Device according to claim 11, wherein the device performs Fourier transformation to transform a measured time course of the magnetic field from a time domain to a frequency domain.

18. Device according to claim 11, further comprising an output device for providing an output signal, which is adapted to indicate the condition of the cannula as at least one of straight, bent, kinked, compressed, broken/severed, coaxial to a longitudinal axis of the syringe, oblique to the longitudinal axis, eccentric to the longitudinal axis.

\* \* \* \* \*